United States Patent
Lee et al.

(10) Patent No.: US 10,088,412 B2
(45) Date of Patent: Oct. 2, 2018

(54) APPARATUS FOR ANALYZING BIO-MATERIAL

(71) Applicant: ELECTRONICS AND TELECOMMUNICATIONS RESEARCH INSTITUTE, Daejeon (KR)

(72) Inventors: Dae-Sik Lee, Daejeon (KR); Moon Youn Jung, Daejeon (KR); Jae-Ki Sim, Daejeon (KR)

(73) Assignee: ELECTRONICS & TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 15/686,081

(22) Filed: Aug. 24, 2017

(65) Prior Publication Data

US 2018/0088030 A1 Mar. 29, 2018

(30) Foreign Application Priority Data

Sep. 27, 2016 (KR) .................. 10-2016-0124278
Feb. 9, 2017 (KR) .................. 10-2017-0018328

(51) Int. Cl.
*G01J 3/46* (2006.01)
*G01N 21/27* (2006.01)
(Continued)

(52) U.S. Cl.
CPC ............. *G01N 21/27* (2013.01); *G01N 21/01* (2013.01); *G01N 2021/0112* (2013.01); *G01N 2021/1742* (2013.01)

(58) Field of Classification Search
CPC ........ G01J 3/46; G01J 3/50; G01J 3/02; G01J 3/524; G01J 3/51
(Continued)

(56) References Cited

U.S. PATENT DOCUMENTS 6,334,688 B1  1/2002  Niwa
7,206,040 B2  4/2007  Kano
(Continued)

FOREIGN PATENT DOCUMENTS

KR   10-0444932 B1   8/2004
KR   10-0875996 B1   12/2008
(Continued)

OTHER PUBLICATIONS

Dae-Sik Lee et al., "A simple and smart telemedicine device for developing regions: a pocket-sized colorimetric reader", Lab Chip, 2011, pp. 120-126, vol. 11, The Royal Society of Chemistry.

*Primary Examiner* — Md M Rahman

(57) ABSTRACT

Provided is an apparatus for analyzing a bio-material. According to an embodiment of the inventive concept, the apparatus may include a light distribution part having grooves, a reflective layer provided on the grooves, and a light emitting part configured to emit light to the light distribution part. The grooves may be recessed from a top surface of the light distribution part, and sidewalls of the grooves may be inclined with respect to the top surface of the light distribution part. The grooves may include a first groove and a second groove. A distance between the light emitting part and the second groove may be greater than that between the light emitting part and the first groove, and a bottom surface of the second groove may be disposed at a level lower than that of a bottom surface of the first groove.

12 Claims, 7 Drawing Sheets

(51) Int. Cl.
*G01N 21/01* (2006.01)
*G01N 21/17* (2006.01)

(58) Field of Classification Search
USPC .......................................................... 356/402
See application file for complete search history.

(56) References Cited

U.S. PATENT DOCUMENTS

| | | |
|---|---|---|
| 8,797,536 B2 | 8/2014 | Lee et al. |
| 8,991,238 B2 | 3/2015 | Lee et al. |
| 2007/0183168 A1* | 8/2007 | Naganawa ............. B60Q 1/085 362/545 |
| 2009/0015815 A1* | 1/2009 | Ohsaki ................... G03B 27/32 355/68 |
| 2009/0194778 A1* | 8/2009 | Huang .................... H01L 33/54 257/98 |
| 2010/0157300 A1 | 6/2010 | Lee et al. |
| 2014/0036480 A1* | 2/2014 | Park ...................... G02B 6/0023 362/97.3 |
| 2015/0009453 A1* | 1/2015 | Cha ....................... G02B 6/0001 349/65 |
| 2015/0176775 A1* | 6/2015 | Gu ............................ F21K 9/60 349/42 |
| 2015/0309244 A1* | 10/2015 | Kim ...................... G02B 6/0076 362/616 |

FOREIGN PATENT DOCUMENTS

| | | |
|---|---|---|
| KR | 10-1179550 B1 | 9/2012 |
| KR | 10-1257298 B1 | 4/2013 |
| KR | 10-1543231 B1 | 8/2015 |

* cited by examiner

APPARATUS FOR ANALYZING BIO-MATERIAL

CROSS-REFERENCE TO RELATED APPLICATIONS

This U.S. non-provisional patent application claims priority under 35 U.S.C. § 119 of Korean Patent Application Nos. 10-2016-0124278, filed on Sep. 27, 2016, and 10-2017-0018328, filed on Feb. 9, 2017, the entire contents of which are hereby incorporated by reference.

BACKGROUND

The present disclosure herein relates to an apparatus for analyzing a bio-material, and more particularly, to a light distribution part of an apparatus for analyzing a bio-material.

As the nanobio-technology (NBT) is the next generation technology relating to diagnosis and treatment of human diseases, its importance is increasing. Studies on devices for simply and rapidly analyzing information about bio-materials are increasing. A user can directly test if there is something abnormal in the body by using a portable apparatus for analyzing a bio-material without going to hospital. For example, diabetes can be measured by analyzing urine with the portable apparatus for analyzing the bio-material. Samples for the above described bio-material are easily collected, and the burden of the test can be reduced for the user. Also, the apparatus for analyzing the bio-material can show results quickly to achieve high usefulness. In order to improve accuracy and reproducibility of the apparatus for analyzing the bio-material, light needs to be uniformly distributed over a strip kit.

SUMMARY

The present disclosure provides an apparatus for analyzing a bio-material, which shows improved accuracy and reproducibility.

The present disclosure also provides a miniaturized apparatus for analyzing a bio-material.

An embodiment of the inventive concept provides an apparatus for analyzing a bio-material, including a light distribution part having grooves; a reflective layer provided on the grooves; and a light emitting part configured to emit light to the light distribution part, wherein the grooves are recessed from a top surface of the light distribution part, sidewalls of the grooves are inclined with respect to the top surface of the light distribution part, the grooves include a first groove and a second groove, a distance between the light emitting part and the second groove is greater than that between the light emitting part and the first groove, and a bottom surface of the second groove is disposed at a level lower than that of a bottom surface of the first groove.

In an embodiment, each of the bottom surface of the first groove and the bottom surface of the second groove may be disposed at a level lower than that of the top surface of the light distribution part.

In an embodiment, the reflective layer may include: a first reflective layer disposed on the first groove; and a second reflective layer disposed on the second groove, wherein the first reflective layer and the second reflective layer expose the top surface of the light distribution part.

In an embodiment, the first groove may be filled with the first reflective layer, and the second groove may be filled with the second reflective layer.

In an embodiment, the reflective layer may cover the sidewalls of the first and second grooves to extend to the top surface of the light distribution part.

In an embodiment, the apparatus may further include: a stage part to which light emitted from the light distribution part is irradiated; and a sensing part provided between the stage part and the light distribution part.

In an embodiment, the apparatus may further include a shielding pattern disposed between the stage part and the light distribution part and disposed in one side of the sensing part.

In an embodiment, the grooves may further include a third groove, a distance between the light emitting part and the third groove may be greater than that between the light emitting part and the second groove, and a bottom surface of the third groove may be disposed at a level lower than that of the bottom surface of the second groove.

In an embodiment, the light distribution part may include a polymer and be transparent.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
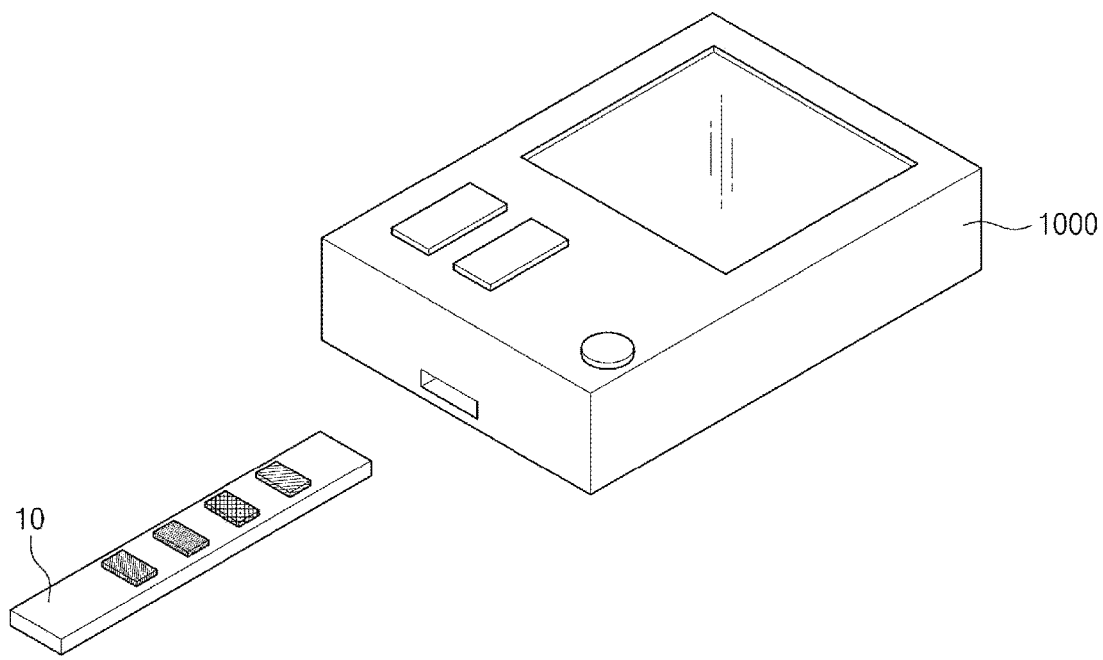
FIG. 1 is a schematic perspective view of an apparatus for analyzing a bio-material according to embodiments of the inventive concept.

Exemplary embodiments of the inventive concept will be described with reference to the accompanying drawings so as to sufficiently understand constitutions and effects of the present disclosure. The present disclosure may, however, be embodied in different forms with various changes and should not be construed as limited to the embodiments set forth herein. Rather, these embodiments are provided so that this disclosure will be thorough and complete, and will fully convey the scope of the present disclosure to those skilled in the art. A person with ordinary skill in the art to which the present disclosure pertains will understand that the inventive concept can be carried out under any appropriate condition.

The terms are used only for explaining embodiments while not limiting of the present disclosure. In this specification, the singular forms are intended to include the plural forms as well, unless the context clearly indicates otherwise.

It will be understood that the terms 'comprises' and/or 'comprising', when used in this specification, specify the presence of stated components, steps, operations and/or elements, but do not preclude the presence or addition of one or more other components, steps, operations and/or elements.

It will be understood that when a film (or layer) is referred to as being 'on' another film (or layer) or substrate, it can be directly on the other film (or layer) or substrate, or intervening films (or layers) may also be present therebetween.

It will be understood that, although the terms first, second, third, etc. may be used herein to describe various regions, films (or layers), these regions and films should not be limited by these terms. These terms are used only to distinguish a predetermined region or film (or layer) from another region or film (or layer). Thus, a first film stated in an embodiment could be termed a second film in another embodiment. Each embodiment described and exemplified herein includes a complementary embodiment thereof. Like reference numerals refer to like elements throughout.

Unless otherwise defined, all terms used in embodiments of the inventive concept have the same meaning as commonly understood by one of ordinary skill in the art to which the present disclosure belongs.

Hereinafter, an apparatus for analyzing a bio-material (hereinafter referred to as a "bio-material analysis apparatus") according to an embodiment of the inventive concept will be described.

Figure 2:
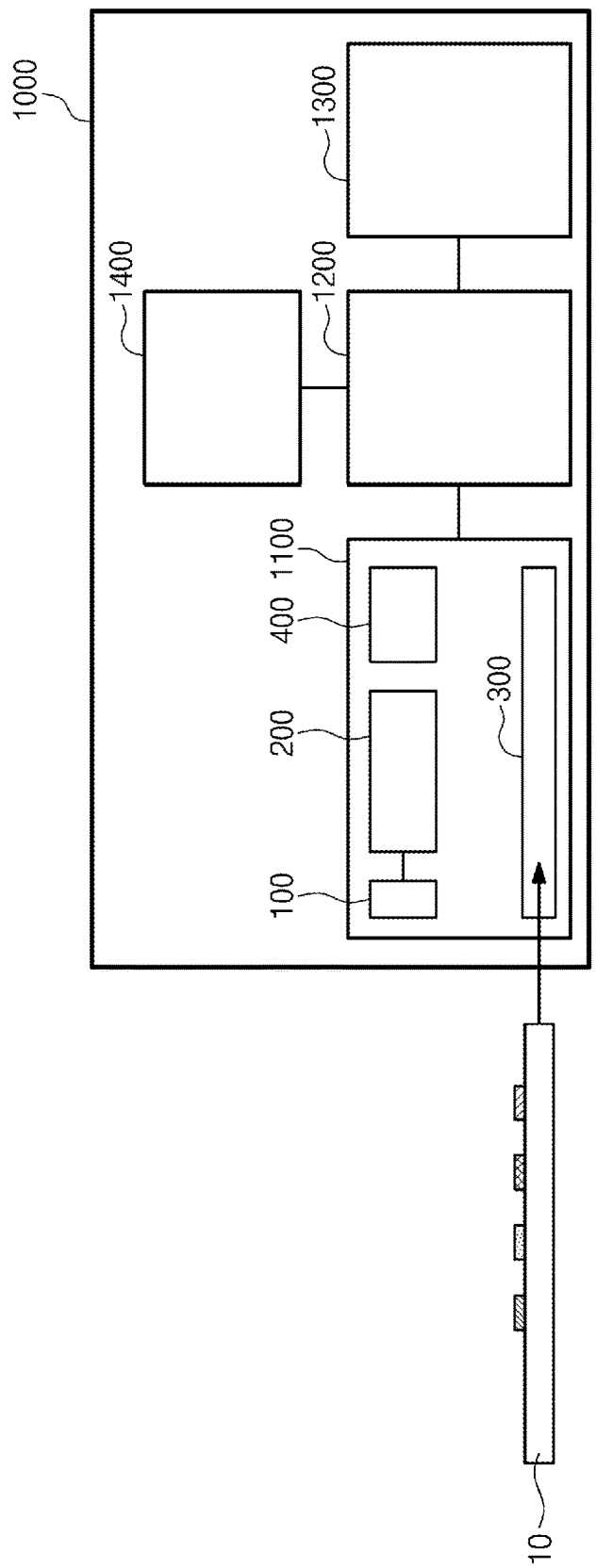
FIG. 2 is a schematic block diagram of an apparatus for analyzing a bio-material according to embodiments of the inventive concept.

FIG. 1 is a schematic perspective view of a bio-material analysis apparatus according to embodiments of the inventive concept. FIG. 2 is a schematic block diagram of the bio-material analysis apparatus according to the embodiments of the inventive concept.

Referring to FIGS. 1 and 2, a bio-material analysis apparatus 1000 may include a measurement unit 1100, a control unit 1200, a display unit 1300, and an information transmission and reception unit 1400. A bio-material may be provided on a strip kit 10. The bio-material may include urine, blood, and saliva. The strip kit 10 may be inserted into the bio-material analysis apparatus 1000. The bio-material analysis apparatus 1000 may measure substances contained in the bio-material and concentrations thereof. For example, the bio-material analysis apparatus 1000 may determine whether glucose is present in the urine and measure a concentration thereof.

The measurement unit 1100 may includes a light emitting part 100, a light distribution part 200, a stage part 300, and a sensing part 400. The strip kit 10 may be disposed on the stage part 300. The light emitting part 100 may emit light to the strip kit 10 through the light distribution part 200. The light emitting part 100 may include a single light source. Accordingly, the bio-material analysis apparatus 1000 may be miniaturized. The light emitted from the light emitting part 100 may include light having different wavelengths. The light emitting part 100 may include light an emitting device such as a liquid crystal display (LCD) device, a field emission display (FED) device, a plasma display panel (PDP) device, or an organic light emitting diode device. The strip kit 10 may reflect the emitted light. For example, the strip kit 10 may absorb light having one wavelength and reflect light having the other wavelength. The other wavelength may be different from the one wavelength. The sensing part 400 may detect the light having the other wavelength emitted from the strip kit 10. The control unit 1200 may provide an electric signal to the light emitting part 100 to control the light emitting part 100. The control unit 1200 may amplify the electrical signal detected by the sensing part 400 to process data. The control unit 1200 may transmit the processed data to the display unit 1300. The display unit 1300 may display the data processed in the control unit 1200.

The data processed in the control unit 1200 may be transmitted to an external device through the information transmission and reception unit 1400. For example, the information transmission and reception unit 1400 may include Bluetooth, near field communication (NFC), Zigbee, Wi-Fi, USB, or a wired and wireless communication module in which a serial communication is available. The external device may include a mobile phone, a smart watch, a tablet PC, a laptop computer, or a personal computer. The information measured in the bio-material analysis apparatus 1000 may be displayed on various external devices without limitation in space. For example, the display unit 1300 of the personal mobile phone may display whether the bio-material is present and the concentration thereof. In this case, the bio-material analysis apparatus 1000 may not include the display unit 1300. Accordingly, the bio-material analysis apparatus 1000 may be further miniaturized. The bio-material analysis apparatus 1000 may have a small size to be portable. For another example, the bio-material analysis apparatus 1000 may be connected to a network system of a hospital through the information transmission and reception unit 1400. Therefore, the user may be provided with a U-healthcare service such as remote health monitoring.

Figure 3:
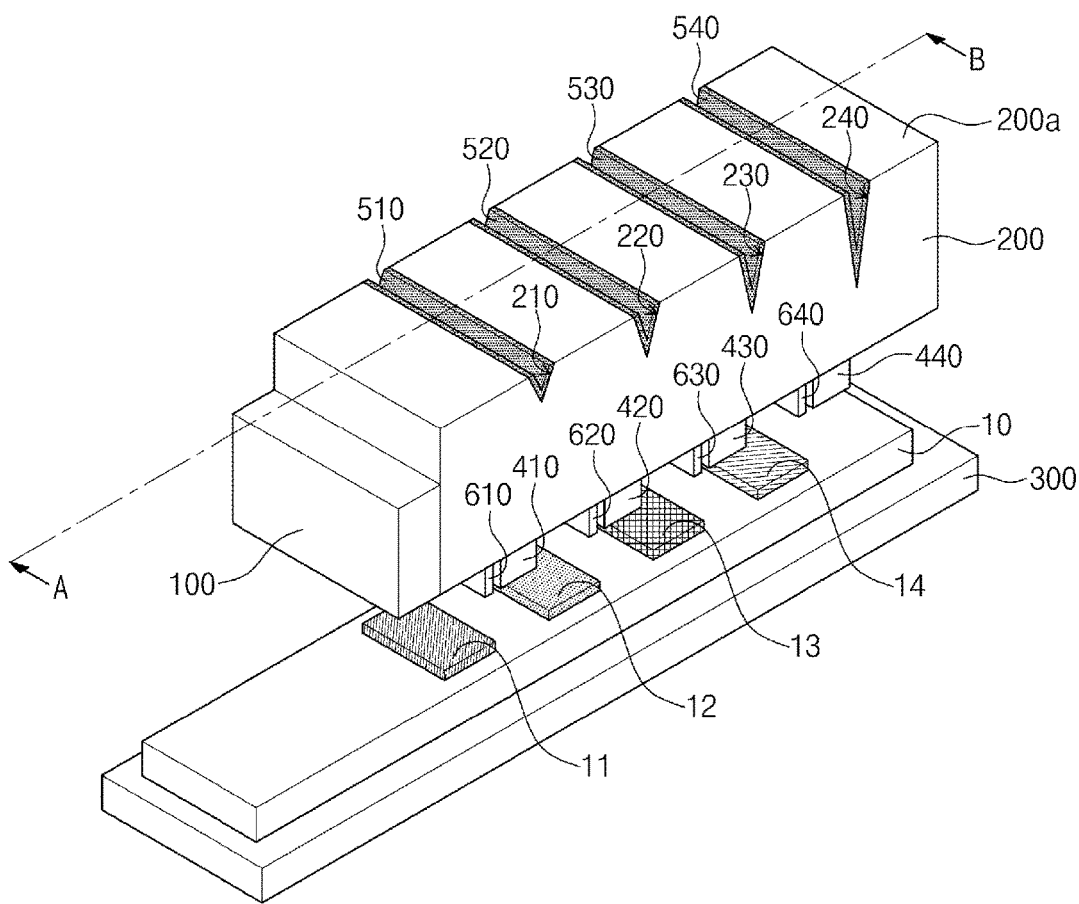
FIG. 3 is a perspective view illustrating a measurement unit of an apparatus for analyzing a bio-material according to an embodiment.
Figure 4:
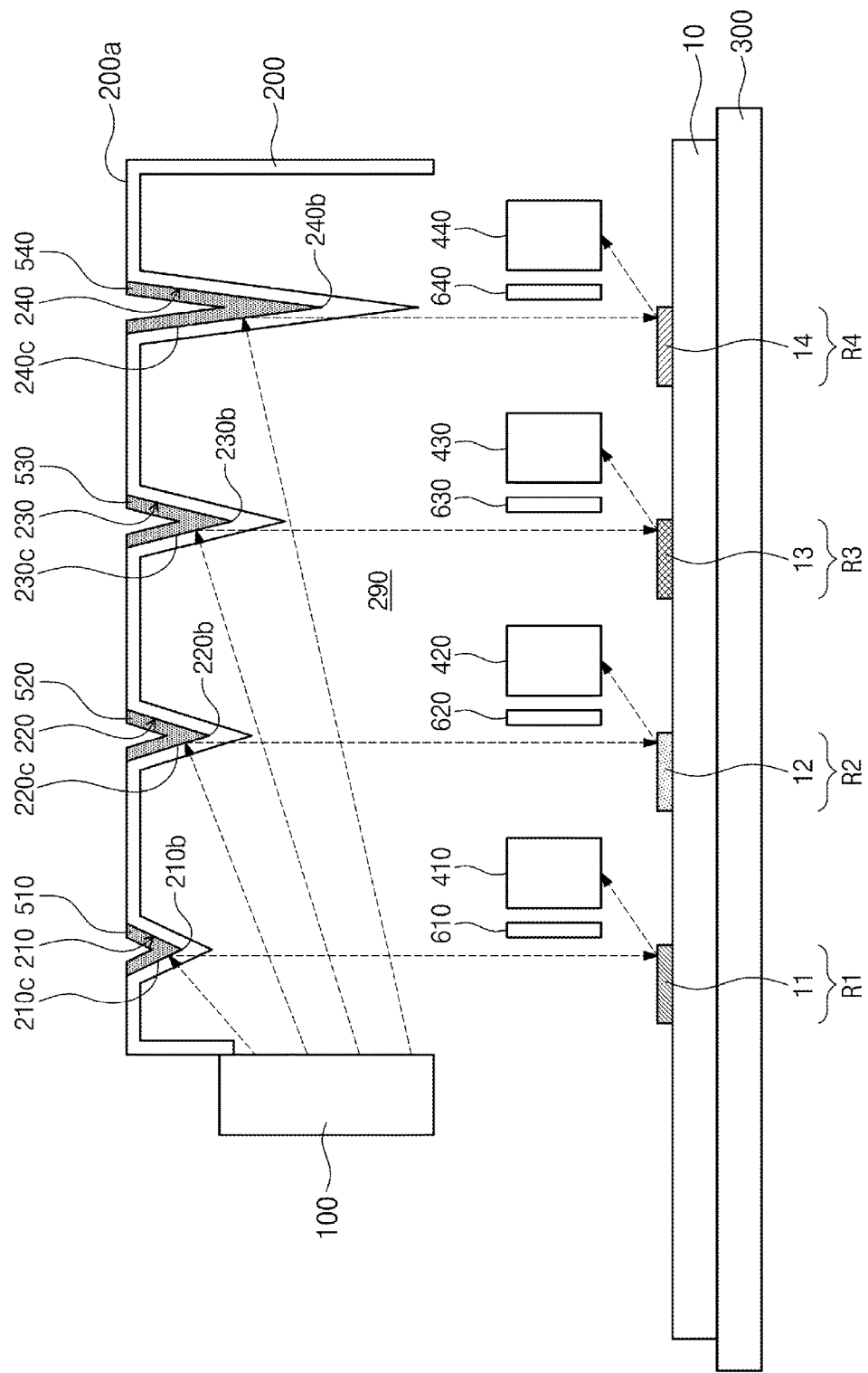
FIG. 4 is a cross-sectional view taken along line A-B of FIG. 3.

FIG. 3 is a perspective view of a measurement unit of a bio-material analysis apparatus according to an embodiment of the inventive concept. FIG. 4 is a cross-sectional view taken along line A-B of FIG. 3. Hereinafter, the duplicated descriptions, which have been described already, will be omitted.

Referring to FIGS. 3 and 4, a measurement unit of the bio-material analysis apparatus may include a light emitting part 100, a light distribution part 200, a stage part 300, sensing parts 410, 420, 430, and 440, and reflective layers 510, 520, 530, and 540. The light emitting part 100 may emit light to the light distribution part 200. The light distribution part 200 may be disposed in one side of the light emitting part 100. The light distribution part 200 may include a cavity 290 therein. The light may be provided within the cavity 290 of the light distribution part 200. The light distribution part 200 may be transparent. The light distribution part 200 may have a polymer. For example, the light distribution part 200 may include cyclo olefin copolymer (COC), polymethylmethacrylate (PMMA), polycarbonate (PC), cyclo olefin polymer (COP), liquid Crystalline Polymers (LCP), polydimethylsiloxane (PDMS), polyamide (PA), polyethylene (PE), polyimide (PI), polypropylene (PP), polyphenylene ether (PPE), polystyrene (PS), polyoxymethylene (POM), polyetheretherketone (PEEK), polyether sulfone (PES), polyethylenephthalate (PET), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), an epoxy based polymer, or a combination thereof.

The light distribution part 200 may include a first groove 210, a second groove 220, a third groove 230, and a fourth groove 240. The grooves 210, 220, 230, and 240 may be provided on a top surface 200a of the light distribution part 200. The grooves 210, 220, 230, and 240 may include sidewalls 210c, 220c, 230c, and 240c. The sidewalls 210c, 220c, 230c, and 240c of the grooves 210, 220, 230, and 240 may be inclined with respect to the top surface 200a of the light distribution part 200. When viewed in a plane, the second groove 220 may be spaced apart from the light emitting part 100 more than the first groove 210 is spaced apart from the light emitting part 100. A distance between the light emitting part 100 and the second groove 220 may be greater than that between the light emitting part 100 and the first groove 210. The third groove 230 may be spaced apart from the light emitting part 100 more than the second groove 220 is spaced apart from the light emitting part 100. The fourth groove 240 may be spaced apart from the light emitting part 100 more than the third groove 230 is spaced apart from the light emitting part 100. The top surface 200a of the light distribution part 200 may be recessed to form the grooves 210, 220, 230, and 240. For example, the grooves 210, 220, 230, and 240 may be formed by injection molding, hot embossing, stereolithography, casting, laser ablation, rapid prototyping, silk screen, or numerical control machining. For another example, the grooves 210, 220, 230, and 240 may be formed by a photolithography process and an etch process. Bottom surfaces 210b, 220b, 230b, and 240b of the grooves 210, 220, 230, and 240 may be disposed at a level lower than that of the top surface 200a of the light distribution part 200. According to embodiments, the grooves 210, 220, 230, and 240 are recessed from the top surface 200a of the light distribution part 200, and thus the light distribution part 200 may be miniaturized.

The first to fourth reflective layers 510, 520, 530, and 540 may be provided on the sidewalls 210c, 220c, 230c, and 240c of the first to fourth grooves 210, 220, 230, and 240, respectively, and the first to fourth grooves 210, 220, 230, and 240 may extend along the sidewalls 210c, 220c, 230c, and 240c, respectively. The reflective layers 510, 520, 530, and 540 may expose the top surface 200a of the light distribution part 200. For example, the reflective layers 510, 520, 530, and 540 may include metal (for example, silver or gold), a mirror, correction fluid, a reflective pigment, or a dielectric material. The reflective layers 510, 520, 530, and 540 may be formed by various methods such as vacuum deposition or coating method. The light may be reflected from the reflective layers 510, 520, 530, and 540 and then emitted to the stage part 300. When viewed in a plane, the stage part 300 may include first to fourth regions R1, R2, R3, and R4.

The second groove 220 may have a depth greater than that of the first groove 210. For example, the bottom surface 220b of the second groove 220 may be provided at a level lower than that of the bottom surface 210b of the first groove 210. In FIGS. 4 to 7, dash lines represent moving paths of the light according to embodiments. A portion of the light may be reflected from the first reflective layer 510 and then emitted to the first region R1 of the stage part 300. Another portion of the light may be incident at a level lower than that of the bottom surface 210b of the first groove 210. The another portion of the light may be reflected from the second reflective layer 520 and then emitted to the second region R2. of the stage part 300. The bottom surface 230b of the third groove 230 may be provided at a level lower than that of the bottom surface 220b of the second groove 220. A further portion of the light may be reflected from the third reflective layer 530 and then emitted to the third region R3. of the stage part 300. The bottom surface 240b of the fourth groove 240 may be provided at a level lower than that of the bottom surface 230b of the third groove 230. A still further portion of the light may be reflected from the fourth reflective layer 540 and then emitted to the fourth region R4. of the stage part 300. Output positions of the light from the light distribution part 200 may be adjusted by controlling the number of the grooves 210, 220, 230, and 240, the degrees of the inclination of the sidewalls 210c, 220c, 230c, and 240c of the grooves 210, 220, 230, and 240, the depths of the grooves 210, 220, 230, and 240, or the refractive indices of the reflective layers 510, 520, 530, and 540. The light distribution part 200 may uniformly provide the light to the first to fourth regions R1, R2, R3, and R4 of the stage part 300 through the grooves 210, 220, 230, and 240. For example, the light provided to the first region R1 of the stage part 300 may have the substantially same intensity as the light provided to the second to fourth regions R2, R3, and R4 of the stage part 300.

The stage part 300 may be disposed under the bottom surface of the light distribution part 200 and spaced apart from the light distribution part 200. The strip kit 10 may be provided on the stage part 300. The strip kit 10 may include a first pad 11, a second pad 12, a third pad 13, and a fourth pad 14. The first pad 11, the second pad 12, the third pad 13, and the fourth pad 14 may be spaced apart from each other on a top surface of the strip kit 10. The first pad 11, the second pad 12, the third pad 13, and the fourth pad 14 may be disposed on the first region R1, the second region R2, the third region R3, and the fourth region R4 of the stage part 300, respectively. The pads 11, 12, 13, and 14 may selectively absorb different substances in the bio-material. When the pads 11, 12, 13, and 14 absorb the substances, the wavelengths of the light reflected from the pads 11, 12, 13, and 14 may change. For example, the first pad 11 absorbs a first substance of the bio-material to emit light having a first wavelength, and the second pad 12 absorbs a second substance of the bio-material to emit light having a second wavelength. The second substance may be different from the first substance, and the second wavelength may be different from the first wavelength. When the light is concentrated on the first pad 11, it may be difficult to measure whether the bio-material is absorbed in the second pad 12. According to embodiments, the light may be uniformly distributed to the first to fourth pads 11, 12, 13, and 14 of the strip kit 10 to improve accuracy and reproducibility of the bio-material analysis apparatus.

The light emitted from the pads 11, 12, 13, and 14 may be irradiated to the sensing parts 410, 420, 430, and 440. Each of the sensing parts 410, 420, 430, and 440 may perform the substantially same function as the sensing part 400 described in FIGS. 1 and 2. The sensing part 410, 420, 430, and 440 may be provided between the stage part 300 and the light distribution part 200. The sensing parts 410, 420, 430, and 440 may be disposed in one sides the pads 11, 12, 13, and 14, respectively, when viewed in a plane. Each of the sensing parts 410, 420, 430, and 440 may include a CMOS image sensor, a photo diode, or a charge coupled device. The first sensing part 410, the second sensing part 420, the third sensing part 430, and the fourth sensing part 440 may sense the light emitted from the first pad 11, the second pad 12, the third pad 13, and the fourth pad 14, respectively. Accordingly, the substances of the bio-material and the concentrations thereof, provided to the strip kit 10, may be measured.

First and fourth shielding patterns 610, 620, 630, and 640 may be further provided under the light distribution part 200. The shielding patterns 610, 620, 630, and 640 may be provided between the stage part 300 and the light distribution part 200. When viewed in a plane, the first shielding pattern 610 may be disposed between the first pad 11 and the first sensing part 410. The second shielding pattern 620 may be disposed between the second pad 12 and the second sensing part 420. The third shielding pattern 630 may be disposed between the third pad 13 and the third sensing part 430. The fourth shielding pattern 640 may be disposed between the fourth pad 14 and the fourth sensing part 440.

The shielding patterns 610, 620, 630, and 640 may include a reflective material. For example, the shielding patterns 610, 620, 630, and 640 may include metal such as silver or gold, whiteout, or a reflective pigment. The shielding patterns 610, 620, 630, and 640 may prevent light noise from being inputted to the sensing parts 410, 420, 430, and 440. Here, the light noise may mean that the light emitted from the light distribution part 200 is directly inputted to the sensing parts 410, 420, 430, and 440 without going through the pads 11, 12, 13, and 14. The light noise may not include information on whether the bio-materials in the pads 11, 12, 13, and 14 are present or not. The accuracy and reproducibility of the bio-material analysis apparatus may be further improved by the light shielding patterns 610, 620, 630, and 640.

Figure 5:
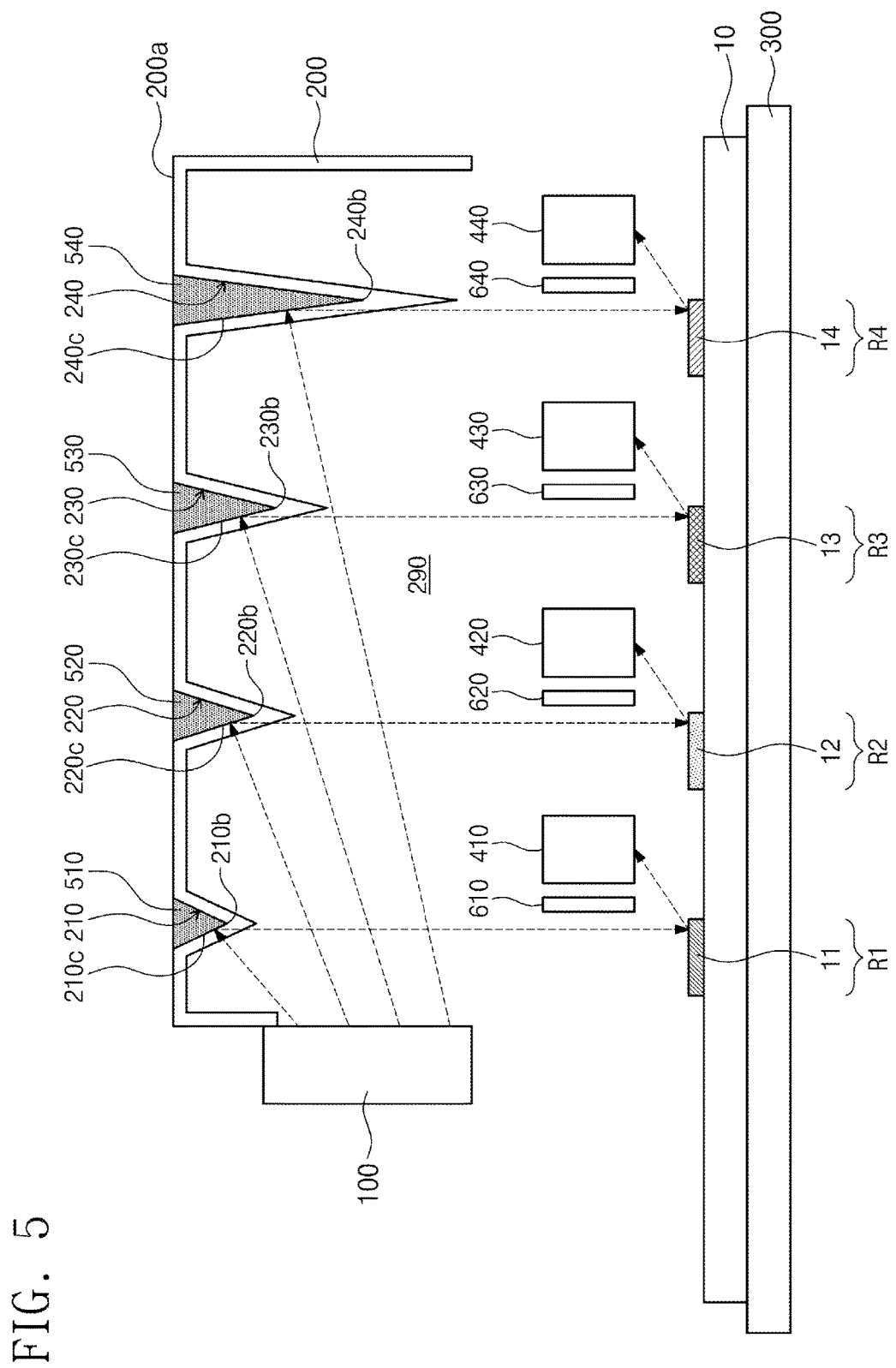
FIG. 5 is a cross-sectional view illustrating a measurement unit of an apparatus for analyzing a bio-material according to another embodiment.

FIG. 5 is a cross-sectional view illustrating a measurement unit of a bio-material analysis apparatus according to another embodiment. Hereinafter, the duplicated descriptions, which have been described already, will be omitted.

Referring to FIG. 5, the bio-material analysis apparatus may include a light emitting part 100, a light distribution part 200, a stage part 300, sensing parts 410, 420, 430, and 440, and reflective layers 510, 520, 530, and 540. First and fourth grooves 210, 220, 230, and 240 may be filled with the first to fourth reflective layers 510, 520, 530, and 540, respectively. The top surfaces of the first to fourth reflective layers 510, 520, 530, and 540 may be provided at a level similar with that of a top surface 200a of the light distribution part 200. The first to fourth reflective layers 510, 520, 530, and 540 may include the substantially same material as described in FIGS. 3 and 4.

Figure 6:
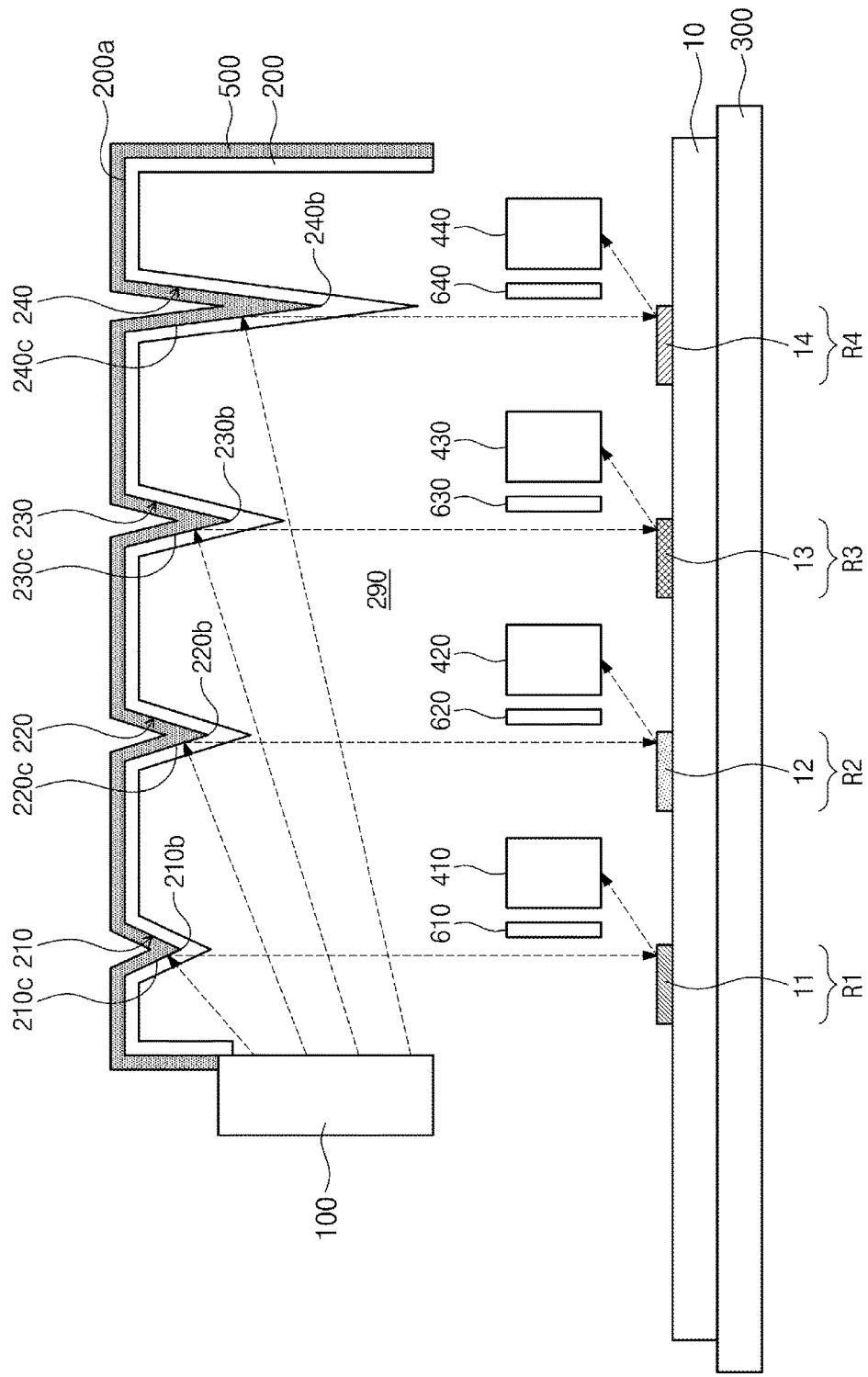
FIG. 6 is a cross-sectional view illustrating a measurement unit of an apparatus for analyzing a bio-material according to a further embodiment.

FIG. 6 is a cross-sectional view illustrating a measurement unit of a bio-material analysis apparatus according to a further embodiment. Hereinafter, the duplicated descriptions, which have been described already, will be omitted.

Referring to FIG. 6, the bio-material analysis apparatus may include a light emitting part 100, a light distribution part 200, a stage part 300, sensing parts 410, 420, 430, and 440, and a reflective layer 500. The reflective layer 500 may be provided on sidewalls 210c, 220c, 230c, and 240c of first to fourth grooves 210, 220, 230, and 240. The reflective layers 500 may further extend to a top surface 200a and a side surface of the light distribution part 200.

Figure 7:
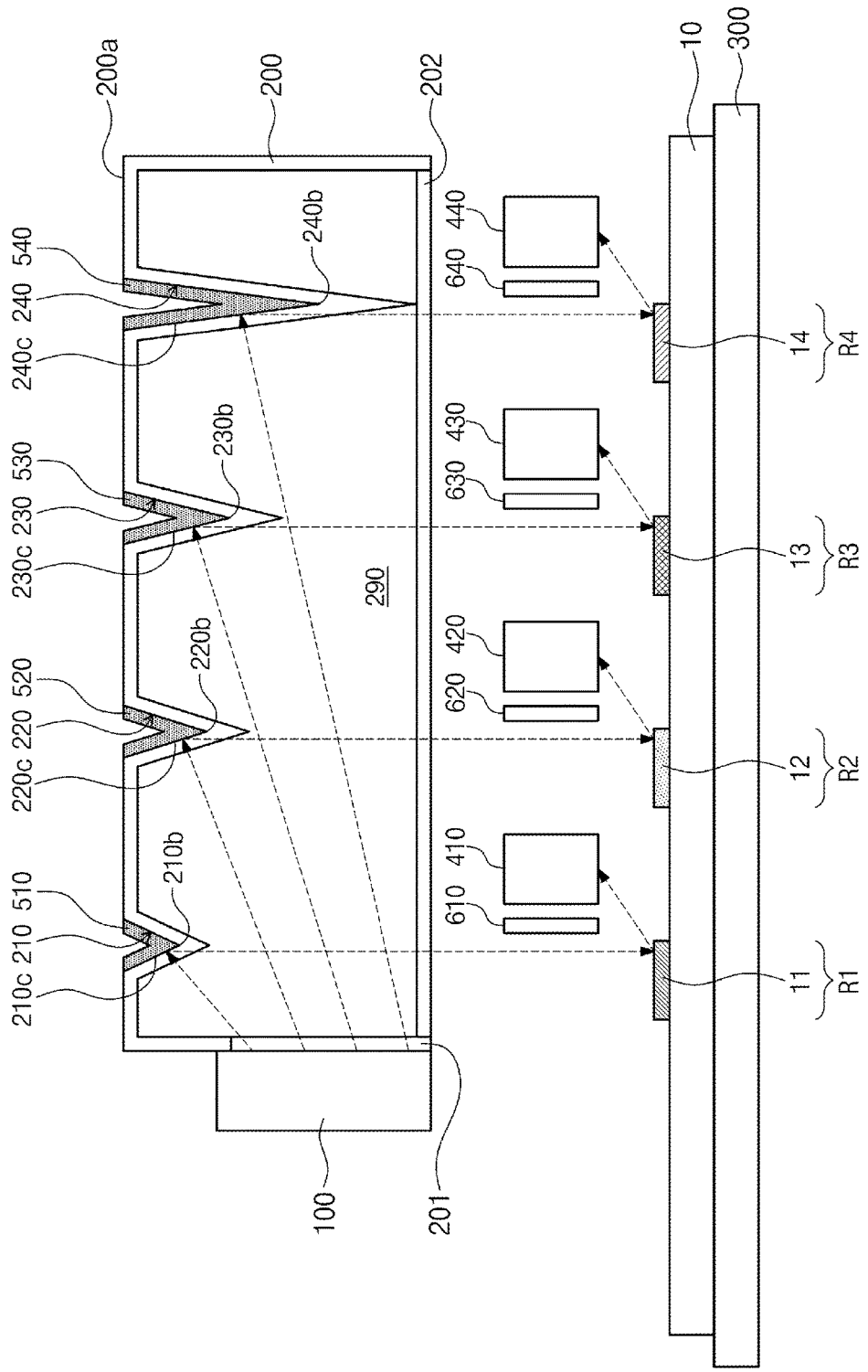
FIG. 7 is a cross-sectional view illustrating a measurement unit of an apparatus for analyzing a bio-material according to a further embodiment.

FIG. 7 is a cross-sectional view illustrating a measurement unit of a bio-material analysis apparatus according to a further embodiment. Hereinafter, the duplicated descriptions, which have been described already, will be omitted.

Referring to FIG. 7, the bio-material analysis apparatus may include a light emitting part 100, a light distribution part 200, a stage part 300, sensing parts 410, 420, 430, and 440, and reflective layers 510, 520, 530, and 540. The light distribution part 200 may include a first transparent film 201 and a second transparent film 202. The first transparent film 201 may be provided between the light emitting part 100 and a cavity 290. The light emitted from the light emitting part 100 may be irradiated in the cavity 290 of the light distribution part 200 through the first transparent film 201. The second transparent film 202 may be provided between the cavity 290 and the stage part 300. The light reflected from the reflective layers 510, 520, 530, and 540 may be emitted on the stage part 300 through the second transparent film 202. The first transparent film 201 and the second transparent film 202 may be manufactured by a separate process from the light distribution part 200 or the same process therewith.

According to the embodiments of the inventive concept, the groove may be provided on the top surface of the light distribution part. The reflective layer may cover the sidewall of the groove. The light irradiated from the light emitting part to the light distribution part may be uniformly emitted on the strip kit by the reflective layer. Accordingly, the accuracy and reproducibility of the bio-material analysis apparatus may be improved.

The groove may be recessed on the top surface of the light distribution part to miniaturize the light distribution part.

The above detailed description of the present disclosure does not intend to limit the present disclosure to the disclosed embodiments and can be used under various different combinations, changes, and conditions without departing from the subject matters of the present disclosure. The appended claims should be appreciated to include another embodiment.

What is claimed is:

1. An apparatus for analyzing a bio-material, the apparatus comprising:
   a light distribution part having first and second grooves recessed from a top surface of the light distribution part, sidewalls of the first and second grooves being inclined with respect to the top surface of the light distribution part;
   a reflective layer disposed on the inclined sidewalls of the first and second grooves; and
   a light emitting part configured to emit light into the light distribution part, the light being reflected by the reflective layer disposed on the inclined sidewalls of the first and second grooves toward a strip kit;
   a first sensor configured to sense a portion of the light that has been reflected by the reflective layer disposed on the first groove and from the strip kit; and
   a second sensor configured to sense a portion of the light that has been reflected by the reflective layer disposed on the second groove and from the strip kit,
   wherein a distance between the light emitting part and the second groove is greater than a distance between the light emitting part and the first groove, and
   wherein a bottom of the second groove is disposed at a level that is lower than a bottom of the first groove.

2. The apparatus of claim 1, wherein each of the bottom of the first groove and the bottom of the second groove is disposed at a lower level than the top surface of the light distribution part.

3. The apparatus of claim 1, wherein the reflective layer comprises:
   a first reflective layer disposed on the first groove; and
   a second reflective layer disposed on the second groove, and
   wherein the first reflective layer and the second reflective layer expose the top surface of the light distribution part.

4. The apparatus of claim 3, wherein the first groove is filled with the first reflective layer, and
   the second groove is filled with the second reflective layer.

5. The apparatus of claim 1, wherein the reflective layer covers the sidewalls of the first and second grooves and extends to the top surface of the light distribution part.

6. The apparatus of claim 1, further comprising:
   a stage part to which the light, which has been reflected from the reflective layer disposed on the inclined sidewalls of the first and second grooves, is emitted, the stage part holding the strip kit; and
   a sensing part provided between the stage part and the light distribution part, the sensing part including the first and second sensors.

7. The apparatus of claim 6, further comprising a shielding pattern disposed between the stage part and the light distribution part and disposed at one side of the sensing part.

8. The apparatus of claim 1, wherein the light distribution part further has a third groove,
   wherein a distance between the light emitting part and the third groove is greater than the distance between the light emitting part and the second groove, and
   wherein a bottom of the third groove is disposed at a lower level than the bottom of the second groove.

9. The apparatus of claim 1, wherein the light distribution part comprises a polymer and is transparent.

10. The apparatus of claim 1, wherein the first sensor is configured to sense a portion of the light that has been reflected from a first pad of the strip kit, and the second sensor is configured to sense a portion of the light that has been reflected from a second pad of the strip kit, the first pad being separate from the second pad.

11. The apparatus of claim 10, wherein the portion of the light that has been reflected from the first pad of the strip kit corresponds to a concentration of a substance on the first pad, and
   wherein the portion of the light that has been reflected from the second pad of the strip kit corresponds to a concentration of the substance on the second pad.

12. The apparatus of claim 1, wherein the light distribution part is transparent, the light being transmitted through the light distribution part.

\* \* \* \* \*